United States Patent
Graziani et al.

(10) Patent No.: US 7,273,874 B2
(45) Date of Patent: Sep. 25, 2007

(54) RAPAMYCIN DERIVATIVES AND THE USES THEREOF IN THE TREATMENT OF NEUROLOGICAL DISORDERS

(75) Inventors: Edmund Idris Graziani, Chestnut Ridge, NY (US); Kevin Pong, Robbinsville, NJ (US); Jerauld Skotnicki, Westfield, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/300,941

(22) Filed: Dec. 15, 2005

(65) Prior Publication Data

US 2006/0135550 A1 Jun. 22, 2006

Related U.S. Application Data

(60) Provisional application No. 60/638,004, filed on Dec. 20, 2004.

(51) Int. Cl.
C07D 498/18 (2006.01)
A61K 31/435 (2006.01)

(52) U.S. Cl. ...................... 514/286; 540/456
(58) Field of Classification Search ............... 540/456; 514/286
See application file for complete search history.

(56) References Cited

U.S. PATENT DOCUMENTS

| | | | |
|---|---|---|---|
| 3,491,092 A | 1/1970 | Grignat et al. | |
| 3,686,238 A | 8/1972 | Zaffaroni et al. | |
| 3,738,980 A | 6/1973 | Bickel et al. | |
| 3,900,465 A | 8/1975 | Cricchio et al. | |
| 3,905,981 A | 9/1975 | Olofson et al. | |
| 4,127,720 A | 11/1978 | Juby et al. | |
| 5,023,262 A | 6/1991 | Caufield et al. | |
| 5,525,610 A | 6/1996 | Caufield et al. | |
| 5,604,294 A | 2/1997 | Luly et al. | |
| 5,696,135 A | 12/1997 | Steiner et al. | |
| 5,717,092 A | 2/1998 | Armistead et al. | |
| 5,780,484 A | 7/1998 | Zelle et al. | |
| 5,798,355 A | 8/1998 | Steiner et al. | |
| 6,015,809 A | 1/2000 | Zhu et al. | |
| 6,187,784 B1 | 2/2001 | Steiner et al. | |
| 6,500,843 B2 | 12/2002 | Steiner et al. | |
| 6,624,302 B2 | 9/2003 | Chu et al. | |
| 2001/0036947 A1 | 11/2001 | Steiner et al. | |
| 2002/0151088 A1 | 10/2002 | Molnar-Kimber et al. | |
| 2004/0224394 A1 | 11/2004 | Katz et al. | |

FOREIGN PATENT DOCUMENTS

| AU | 9516257 | 10/1995 |
|---|---|---|
| DE | 1445742 | 12/1968 |
| DE | 1545824 | 12/1969 |
| DE | 4021404 A1 | 1/1992 |
| EP | 0343560 A2 | 11/1989 |
| EP | 0 475 577 A1 | 8/1991 |
| EP | 0778023 A1 | 6/1997 |
| GB | 2249027 A | 4/1992 |
| JP | 08333256 | 12/1996 |
| WO | WO-91/19495 | 12/1991 |
| WO | WO-92/13862 | 8/1992 |
| WO | WO-93/04679 | 3/1993 |
| WO | WO-93/04680 | 3/1993 |
| WO | WO-94/02136 | 2/1994 |
| WO | WO-94/02485 | 2/1994 |
| WO | WO-94/25022 | 11/1994 |
| WO | WO-96/40140 | 12/1996 |
| WO | WO-99/62483 | 12/1999 |

(Continued)

OTHER PUBLICATIONS

Cantley et al., "New Insights into Tumor Suppression: PTEC Suppresses Tumor Formation by Restraining the Phosphoinositide 3-Kinase/AKT Pathway" Proc. Natl. Acad. Sci. USA, 96:4240-4245 (Apr. 1999).

Ali et al., "Mutational Spectra of PTEN/MMAC1 Gene: A Tumor Suppressor with Lipid Phosphatase Activity", J. Natl. Cancer. Inst., 91(22):1922 (Nov. 17, 1999).

Navé et al., "Mammalian Target of Rapamycin is a Direct Target for Protein Kinase B: Identification of a Convergence Point for Opposing Effects of Insulin and Amino-Acid Deficiency on Protein Translation" Biochem. J. 344:427-431 (Dec. 1, 1999).

Scott et al., "Evidence of Insulin-Stimulated Phosphorylation and Activation of the Mammalian Target of Rapamycin Mediated by a Protein Kinase B Signaling Pathway" Proc. Nat. Acad. Sci. USA, 95:7772-7777 (Jun. 1998).

(Continued)

*Primary Examiner*—Bruck Kifle
(74) *Attorney, Agent, or Firm*—Arnold S. Milowsky; Howson & Howson LLP

(57) ABSTRACT

The present invention provides compounds of the following structure, wherein $R_1$-$R_9$, $R_{15}$, and n are defined herein.

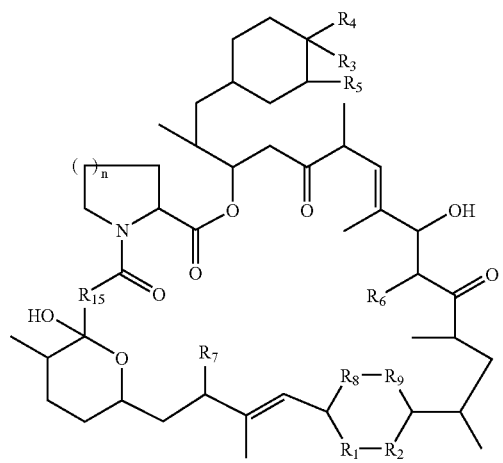

These compounds are useful in treating neurological disorders or complications due to stroke or head injury, and as neuroprotective and neuroregenerative agents.

18 Claims, No Drawings

FOREIGN PATENT DOCUMENTS

| | | |
|---|---|---|
| WO | WO-00/09109 | 2/2000 |
| WO | WO-00/09510 | 2/2000 |
| WO | WO-00/34239 | 6/2000 |
| WO | WO-01/18006 A1 | 3/2001 |
| WO | WO-01/34816 A1 | 5/2001 |
| WO | WO-01/87884 A2 | 11/2001 |
| WO | WO-03/018573 A1 | 3/2003 |
| WO | WO-03/018574 A1 | 3/2003 |
| WO | WO-2004/007709 A2 | 1/2004 |

OTHER PUBLICATIONS

Steiner et al., Neurotrophic Actions of Nonimmunosuppressive Analogues of Immunosuppressive Drugs FK506, Rapamycin and Cyclosporin Nat. Med., 3(4):421 (Apr. 1997).

Gold et al., "Neuroimmunophilin Ligands: The Development of Novel Neuroregenerative/Neuroprotective Compounds", Curr. Topics Med. Chem., 3:1368 (2003).

Birge et al., "A Role for Schwann Cells in the Neuroregenerative Effects of a Non-Immunosuppressive FK506 Derivative, JNJ460", Neuroscience, 124:351-366 (2004).

Tanaka et al., "Possibility of Non-Immunosuppressive Immunophilin Ligands as Potential Therapeutic Agents for Parkinson's Disease" Curr. Pharm. Design, 10:669-677 (2004).

Snyder et al, Immunophilins and the Nervous System, Nature Medicine, vol. 1, No. 1, pp. 32-37, (Jan. 1995).

Holt et al, Structure-Activity Studies of Synthetic FKBP Ligands as Peptidyl-Prolyl Isomerase Inhibitors, Biorganic & Medicinal Chemistry Letters, vol. 4, No. 2, pp. 315-320, (1994).

Pong et al., "Therapeutic Implications for Immunophilin Ligands in the Treatment of Neurodegenerative Diseases" Curr. Drug Targets—CNS & Neurolog. Disorders, 2(6):349 (Dec. 2003).

Ocain et al., "A Nonimmunosuppressive Triene-Modified Rapamycin Analog is a Potent Inhibitor of Peptidyl Prolyl Cis-Trans Isomerase", Biochem. Biophys. Rse. Commun. 192(3):1340 (May 14, 1993).

Dickman et al., "Antifungal Rapamycin Analogues with Reduced Immunosuppressive Activity", Bioorg. & Med. Chem. Lett. 10(13):1405-1408 (Jul. 3, 2000).

Li et al., "Analysis of the Energetics of Gas-Phase Immunophilin-Ligand Complexes by Ion Spray Mass Spectrometry", J. Am. Chem. Soc., 116(17):7487 (1994).

Grigat et al., "2-Sulphonamido- and 2-Sulphonylhydrazido-benzoxazinones", English language Abstract of DE 1,545,824, (Jun. 21, 1965).

Nussbaumer et al., "New Tricyclic Heteroatom Containing Compounds for Arthritis", English language Abstract of DE 4,021,404 (Jul. 5, 1990).

RAPAMYCIN DERIVATIVES AND THE USES THEREOF IN THE TREATMENT OF NEUROLOGICAL DISORDERS

CROSS-REFERENCE TO RELATED APPLICATIONS

This application claims the benefit under 35 USC 119(e) of prior U.S. Provisional Patent Application No. 60/638,004, filed Dec. 20, 2004.

BACKGROUND OF THE INVENTION

The present invention provides rapamycin derivatives and their use in the treatment of neurological disorders.

Ischemic stroke, which accounts for 83% of all stroke cases (the remaining 17% are of the hemorrhagic-type) occurs in approximately 700,000 Americans each year, which equates to roughly 1 stroke every 45 seconds. Ischemic strokes occur as a result of an obstruction within a blood vessel supplying blood to the brain. The underlying condition for this type of obstruction is the development of fatty deposits lining the vessel walls, called atherosclerosis. These fatty deposits can cause two types of obstruction: 1) cerebral thrombosis, which refers to a thrombus (blood clot) that develops at the clogged part of the vessel and 2) cerebral embolism, which refers generally to a blood clot that forms at another location in the circulatory system, usually the heart and large arteries of the upper chest and neck. A portion of the blood clot breaks loose, enters the bloodstream and travels through the brain's blood vessels until it reaches vessels too small to let it pass. Current therapies to treat ischemic stroke are limited. To date, the only approved drug for ischemic stroke is recombinant tissue plasminogen activator (rt-PA), rt-PA, which acts as a thrombolytic, has a limited therapeutic window of opportunity (3 hours), therefore allowing only 1-2% of all stroke patients to receive treatment. There are no marketed neuroprotectants agents for ischemic stroke.

Parkinson's disease (PD) is a neurodegenerative disease that is neuropathologically characterized by the selective degeneration of dopaminergic (DAergic) neurons of the substantia nigra. PD is a progressive disease with a mean age at onset of 55, although 15% of patients are diagnosed before the age of 50. It is estimated that 1.5 million Americans have PD. Some of the classical signs of PD are resting tremor on one side of the body, generalized slowness of movement (bradykinesia), stiffness of limbs (rigidity), gait or balance problems (postural dysfunction). Current PD medications treat symptoms, whereas none prevent or retard DAergic neuron degeneration.

Given their clinical importance, prototypical molecules that clearly exhibit both neuroprotective and/or neuroregenerative activities have been highly sought after. Neurotrophins are a family of proteins that have extraordinary therapeutic properties in pre-clinical models of neurodegeneration. Although experimentally promising, clinical development of neurotrophins was met with severe obstacles and setbacks, such as the inability to deliver these large proteins to target population of neurons, instability of the proteins, and non-specific activity.

What is needed in the art are further compounds useful in treating neurological disorders.

SUMMARY OF THE INVENTION

In one aspect, the present invention provides novel compounds useful in treating, and in the preparation of medicaments useful in the treatment of, neurological disorders.

In another aspect, the present invention provides novel neuroprotective agents.

In yet a further aspect, the present invention provides rapamycin derivatives, and pharmaceutically acceptable salts, prodrugs, and metabolites thereof.

In another aspect, the present invention provides methods of preparing rapamycin derivatives.

In a further aspect, the present invention provides methods of treating neurological disorders, and the use of a compound of the invention in the preparation of a medicament therefor.

In still another aspect, the present invention provides methods of treating complications due to stroke or head trauma, and the use of a compound of the invention in the preparation of a medicament therefor.

Other aspects and advantages of the present invention are described further in the following detailed description of the preferred embodiments thereof.

DETAILED DESCRIPTION OF THE INVENTION

The present invention provides novel rapamycin derivatives which are useful as neuroprotective agents, particularly in compositions for use in treating neurological disorders. The neurological disorder, including, e.g., a neurodegenerative or neuromuscular degenerative condition, can be a result of a genetic disorder present at birth, a disorder developed during the lifespan of an individual, e.g., stroke, and/or the result of physical trauma e.g., head, spinal injury, or injury to the peripheral nervous system.

Thus, a compound of the invention may be useful in ameliorating the symptoms of a preexisting neurological disorder or preventing further neuro- and/or neuromuscular degeneration. In some embodiments, the neuroprotective agents of the invention can be used to delay the onset of symptoms associated with a neurological disorder.

I. Compounds of the Invention

In one embodiment, the present invention provides rapamycin derivatives of the formula I:

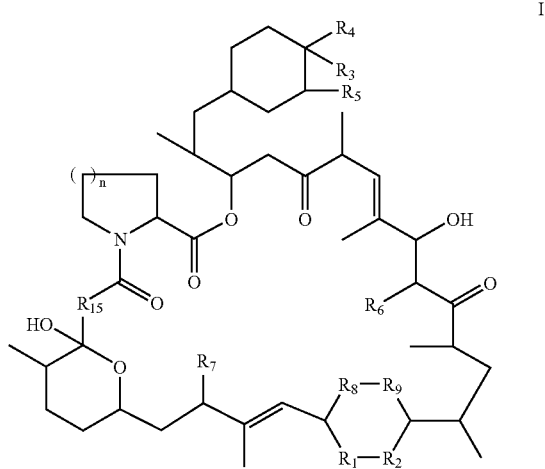

$R_1$ and $R_2$ are the same or different and are selected from among $CR_{16}R_{17}$ and $CR_{18}R_{19}$. $R_3$ and $R_4$ are (a) independently selected from among H, OH, O(C$_1$ to C$_6$ alkyl), O(substituted C$_1$ to C$_6$ alkyl), O(acyl), O(aryl), O(substituted aryl), and halogen; or (b) are taken together to form a double bond to O. R$_5$, R$_6$ and R$_7$ are independently selected among H, OH and OCH$_3$. R$_8$ and R$_9$ are connected through a (i) single bond and are CH$_2$ or (ii) double bond and are CH. R$_{15}$ is selected from among C═O, CHOH and CH$_2$. R$_{16}$ and R$_{17}$ are selected from among H, C$_1$ to C$_6$ alkyl, C$_1$ to C$_6$ substituted alkyl, aryl, substituted aryl, acyl, CF$_3$, CN, and NO$_2$. R$_{18}$ and R$_{19}$ are independently selected from among H, C$_1$ to C$_6$ alkyl, C$_1$ to C$_6$ substituted alkyl, aryl, substituted aryl, acyl, CF$_3$, CN, and NO$_2$ or R$_{17}$ and R$_{18}$ are taken together to form a carbon-based or heterocyclic 5- to 7-membered ring. Further, n is 1 or 2.

Additional compounds that can be prepared according to the present invention include compounds of the following structure:

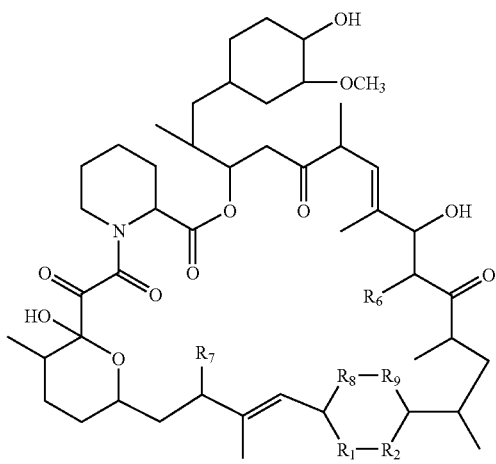

where R$_1$, R$_2$, and R$_6$-R$_9$ are defined as noted above.

In one embodiment, the present invention provides compounds where R$_{17}$ and R$_{18}$ are taken together to form a carbon-based or heterocyclic 5- to 7-membered ring. Other examples of R$_{17}$ and R$_{18}$ include where each is an acyl substituted by alkoxy, e.g., —COOEt. R$_{16}$ and R$_{19}$ may each be CN. In another embodiment, the present invention provides compounds where R$_8$ and R$_9$ are bound through a single bond. In a further embodiment, the present invention provides compounds where R$_3$ or R$_4$ is OH. In yet another embodiment, the present invention provides compounds where R$_3$ or R$_4$ is —O(acyl) preferably where the substituted acyl is —C(O)-optionally substituted alkyl, in particular where alkyl can be straight or branched and optionally substituted, e.g. by heterocyclic such as aromatic heterocyclic such as pyridyl. An example is:

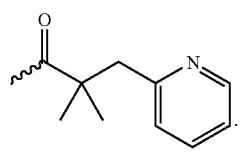

In still a further embodiment, the present invention provides compounds where R$_5$, R$_6$, and R$_7$ are OCH$_3$. In another embodiment, the present invention provides compounds where n is 2. In yet a further embodiment, the present invention provides compounds where R$_{15}$ is C═O.

The compounds of the invention can contain one or more asymmetric carbon atoms and some of the compounds can contain one or more asymmetric (chiral) centers and can thus give rise to optical isomers and diastereomers. While shown without respect to stereochemistry, when the compounds can contain one or more chiral centers, preferably at least one of the chiral centers is of S-stereochemistry. Thus, the invention includes such optical isomers and diastereomers; as well as the racemic and resolved, enantiomerically pure stereoisomers; as well as other mixtures of the R and S stereoisomers, and pharmaceutically acceptable salts, hydrates, metabolites, and prodrugs thereof.

The term "alkyl" is used herein to refer to both straight- and branched-chain saturated aliphatic hydrocarbon groups having 1 to 10 carbon atoms, and desirably about 1 to 8 carbon atoms. The term "alkenyl" is used herein to refer to both straight- and branched-chain alkyl groups having one or more carbon-carbon double bonds and containing about 2 to 10 carbon atoms. In one embodiment, the term alkenyl refers to an alkyl group having 1 or 2 carbon-carbon double bonds and having 2 to about 6 carbon atoms. The term "alkynyl" group is used herein to refer to both straight- and branched-chain alkyl groups having one or more carbon-carbon triple bond and having 2 to 8 carbon atoms. In one embodiment, the term alkynyl refers to an alkyl group having 1 or 2 carbon-carbon triple bonds and having 2 to 6 carbon atoms.

The term "cycloalkyl" is used herein to refer to an alkyl group as previously described that is cyclic in structure and has about 4 to 10 carbon atoms, or about 5 to 8 carbon atoms.

The terms "substituted alkyl", "substituted alkenyl", and "substituted alkynyl" refer to alkyl, alkenyl, and alkynyl groups, respectively, having one or more substituents including, without limitation, halogen, CN, OH, NO$_2$, amino, aryl, heterocyclic, alkoxy, aryloxy, alkylcarbonyl, alkylcarboxy, and arylthio, which groups can be optionally substituted. These substituents can be attached to any carbon of an alkyl, alkenyl, or alkynyl group provided that the attachment constitutes a stable chemical moiety.

The term "aryl" as used herein refers to an aromatic system, e.g., of 6-20 carbon atoms, which can include a single ring or multiple aromatic rings fused or linked together where at least one part of the fused or linked rings forms the conjugated aromatic system. The aryl groups can include, but are not limited to, phenyl, naphthyl, biphenyl, anthryl, tetrahydronaphthyl, phenanthryl, indene, benzonaphthyl, fluorenyl, and carbazolyl.

The term "substituted aryl" refers to an aryl group which is substituted with one or more substituents including halogen, CN, OH, NO$_2$, amino, alkyl, cycloalkyl, alkenyl, alkynyl, alkoxy, aryloxy, alkyloxy, alkylcarbonyl, alkylcarboxy, aminoalkyl, and arylthio, which groups can be optionally substituted. In one embodiment, a substituted aryl group is substituted with 1 to 4 substituents including halogen, CN, OH, NO$_2$, amino, alkyl cycloalkyl, alkenyl, alkynyl, alkoxy, aryloxy, alkyloxy, alkylcarbonyl, alkylcarboxy, aminoalkyl, and arylthio.

The term "heterocyclic" as used herein refers to a stable 4- to 7-membered monocyclic or multicyclic heterocyclic ring which is saturated, partially unsaturated, or wholly unsaturated, including aromatic such as pyridyl. The heterocyclic ring has carbon atoms and one or more heteroatoms including nitrogen, oxygen, and sulfur atoms. In one embodiment, the heterocyclic ring has 1 to 4 heteroatoms in the backbone of the ring. When the heterocyclic ring contains nitrogen or sulfur atoms in the backbone of the ring, the nitrogen or sulfur atoms can be oxidized. The term "heterocyclic" also refers to multicyclic rings, e.g., of 9 to 20 ring members in which a heterocyclic ring is fused to an aryl ring. The heterocyclic ring can be attached to the aryl ring through a heteroatom or carbon atom, provided the resultant heterocyclic ring structure is chemically stable.

A variety of heterocyclic groups are known in the art and include, without limitation, oxygen-containing rings, nitrogen-containing rings, sulfur-containing rings, mixed heteroatom-containing rings, fused heteroatom containing rings, and combinations thereof. Oxygen-containing rings include, but are not limited to, furyl, tetrahydrofuranyl, pyranyl, pyronyl, and dioxinyl rings. Nitrogen-containing rings include, without limitation, pyrrolyl, pyrazolyl, imidazolyl, triazolyl, pyridyl, piperidinyl, 2-oxopiperidinyl, pyridazinyl, pyrimidinyl, pyrazinyl, piperazinyl, azepinyl, triazinyl, pyrrolidinyl, and azepinyl rings. Sulfur-containing rings include, without limitation, thienyl and dithiolyl rings. Mixed heteroatom containing rings include, but are not limited to, oxathiolyl, oxazolyl, thiazolyl, oxadiazolyl, oxatriazolyl, dioxazolyl, oxathiazolyl, oxathiolyl, oxazinyl, oxathiazinyl, morpholinyl, thiamorpholinyl, thiamorpholinyl sulfoxide, oxepinyl, thiepinyl, and diazepinyl rings. Fused heteroatom-containing rings include, but are not limited to, benzofuranyl, thionapthene, indolyl, benazazolyl, purindinyl, pyranopyrrolyl, isoindazolyl, indoxazinyl, benzoxazolyl, anthranilyl, benzopyranyl, quinolinyl, isoquinolinyl, benzodiazonyl, naphthylridinyl, benzothienyl, pyridopyridinyl, benzoxazinyl, xanthenyl, acridinyl, and purinyl rings.

The term "substituted heterocyclic" as used herein refers to a heterocyclic group having one or more substituents including halogen, CN, OH, NO$_2$, amino, alkyl, cycloalkyl, alkenyl, alkynyl, alkoxy, aryloxy, alkyloxy, alkylcarbonyl, alkylcarboxy, aminoalkyl, and arylthio, which groups can be optionally substituted. In one embodiment, a substituted heterocyclic group is substituted with 1 to 4 substituents.

The term "acyl" refers to a —C(O)— group, which is substituted at the carbon atom. The acyl group can be substituted or a terminal acyl group such as an HC(O)— group. The substituents can include any substituents noted above for alkyl groups, viz. one or more substituents including, without limitation, halogen, CN, OH, NO$_2$, amino, aryl, heterocyclic, alkoxy, aryloxy, alkylcarbonyl, alkylcarboxy, and arylthio, which groups can be optionally substituted. Examples include —C(O)-alkoxy (eg. —OMe or —OEt) or —C(O)-alkyl where alkyl can be straight or branched and optionally substituted e.g., by heterocyclic (such as pyridyl).

The term "alkoxy" as used herein refers to the O(alkyl) group, where the point of attachment is through the oxygen-atom and the alkyl group is optionally substituted.

The term "aryloxy" as used herein refers to the O(aryl) group, where the point of attachment is through the oxygen-atom and the aryl group is optionally substituted.

The term "alkyloxy" as used herein refers to the alkylOH group, where the point of attachment is through the alkyl group.

The term "arylthio" as used herein refers to the S(aryl) group, where the point of attachment is through the sulfur-atom and the aryl group can be optionally substituted.

The term "alkylcarbonyl" as used herein refers to the C(O)(alkyl) group, where the point of attachment is through the carbon-atom of the carbonyl moiety and the alkyl group is optionally substituted.

The term "alkylcarboxy" as used herein refers to the C(O)O(alkyl) group, where the point of attachment is through the carbon-atom of the carboxy moiety and the alkyl group is optionally substituted.

The term "aminoalkyl" as used herein refers to both secondary and tertiary amines where the point of attachment is through the nitrogen-atom and the alkyl groups are optionally substituted. The alkyl groups can be the same or different.

The term "halogen" as used herein refers to Cl, Br, F, or I groups.

II. Methods of Preparing the Compounds of the Invention

The rapamycin derivatives of formula I of the present invention are prepared from a rapamycin starting material. In one embodiment, the rapamycin starting material includes, without limitation, rapamycin, norrapamycin, deoxorapamycin, desmethylrapamycins, or desmethoxyrapamycin, or pharmaceutically acceptable salts, prodrugs, or metabolites thereof. However, one of skill in the art would readily be able to select a suitable rapamycin starting material that can be utilized to prepare the novel rapamycin derivatives of the present invention.

The term "desmethylrapamycin" refers to the class of rapamycin compounds which lack one or more methyl groups. Examples of desmethylrapamycins that can be used according to the present invention include 3-desmethylrapamycin (U.S. Pat. No. 6,358,969), 7-O-desmethyl-rapamycin (U.S. Pat. No. 6,399,626), 17-desmethylrapamycin [U.S. Pat. No. 6,670,168], and 32-O-desmethylrapamycin, among others.

The term "desmethylrapamycin" refers to the class of rapamycin compounds which lack one or more methoxy groups and includes, without limitation, 32-desmethoxyrapamycin.

The rapamycin derivatives of formula I of the present invention are therefore prepared by combining a rapamycin starting material and an optionally substituted olefin. The term olefin refers to a molecule that contains a double bond. A variety of olefins can be utilized in the present invention and can readily be selected by one of skill in the art and include diethylfumarate, among others including any olefin sufficiently activated with electron-withdrawing substituents to undergo a [4+2] cycloaddition at temperatures up to 50° C. One of skill in the art would readily be able to select the amount of olefin that would be effective in preparing the rapamycin derivatives of the present invention. In one embodiment, an excess of the olefin is utilized, e.g., a 3:1 ratio of olefin to rapamycin starting material. However, even a 1:1 or 2:1 ratio of olefin to rapamycin starting material can be utilized as determined by one of skill in the art.

The olefin and rapamycin starting material is combined in a solvent. The solvent preferably dissolves the olefin and/or rapamycin on contact, or dissolves the olefin and rapamycin as the reaction proceeds. Solvents that can be utilized in the present invention include, without limitation, dimethylformamide, dioxane such as p-dioxane, chloroform, alcohols such as methanol and ethanol, ethyl acetate, water, acetonitrile, tetrahydrofuran, dichloromethane, and toluene, or combinations thereof. However, one of skill in the art would readily be able to select a suitable solvent based upon the solubility of the rapamycin starting material and olefin, as well as the reactivity of the solvent with the same. The amount of solvent utilized depends upon the scale of the reaction and specifically the amount of rapamycin starting material and olefin present in the reaction mixture. One of skill in the art would readily be able to determine the amount of solvent required.

Typically, the solution containing the olefin, rapamycin starting material, and solvent is maintained at elevated temperatures, and preferably a temperature that does not promote decomposition of the rapamycin and olefin. In one embodiment, the solution is maintained at a temperature of about 30 to about 80° C., and preferably about 50° C. The components are heated for a period of time sufficient to permit reaction between the rapamycin starting material and olefin. One of skill in the art using known techniques would readily be able to monitor the progress of the reaction during heating and thereby determine the amount of time required to perform the reaction. In one embodiment, the rapamycin and olefin are combined with a solvent and maintained at a temperature of about 50° C.

Isolation and purification of the rapamycin derivative is well within one of skill in the art and include chromatography including, without limitation, and recrystallization, high performance liquid chromatography (HPLC) such as reverse phase HPLC, and normal phase HPLC, and size-exclusion chromatography.

Once the rapamycin derivative is obtained, it can be reduced to form a more saturated rapamycin derivative. One of skill in the art would readily be able to select a suitable reducing agent for use in the present invention. In one embodiment, reduction of the rapamycin derivative can be effected using a hydrogenation agent. One of skill in the art would readily be able to select a suitable hydrogenation agent for use in the present invention. Typically, transition metal catalysts or transition metals on a support, preferably a carbon support, among others, in the presence hydrogen gas, are utilized to carry out the reduction. In another embodiment, the reduction is performed using palladium metal on carbon in the presence of hydrogen gas.

Reduction of the rapamycin derivative is typically carried out in a solvent. A variety of solvents can be utilized in the reduction and include, without limitation, alcohols such as methanol. However, one of skill in the art would readily be able to select a suitable solvent for use in the present invention and depending on the hydrogenation catalyst and rapamycin derivative being reduced. The amount of solvent depends on the scale of the reaction, and specifically the amount of rapamycin derivative being reduced.

The amount of hydrogenation agent utilized in the present invention can readily be determined by one of skill in the art. However, one of skill in the art would be able to determine and adjust the amount of hydrogenation agent necessary to perform the reduction and to form the more saturated rapamycin derivatives of the present invention. Further, a variety of apparatuses can be utilized to perform the hydrogenation of the present invention and include Parr apparatuses, among others. The selection of the particular apparatus for the hydrogenation is well within one of skill in the art.

In one embodiment, the rapamycin derivatives of the present invention are prepared as summarized in Scheme 1 below:

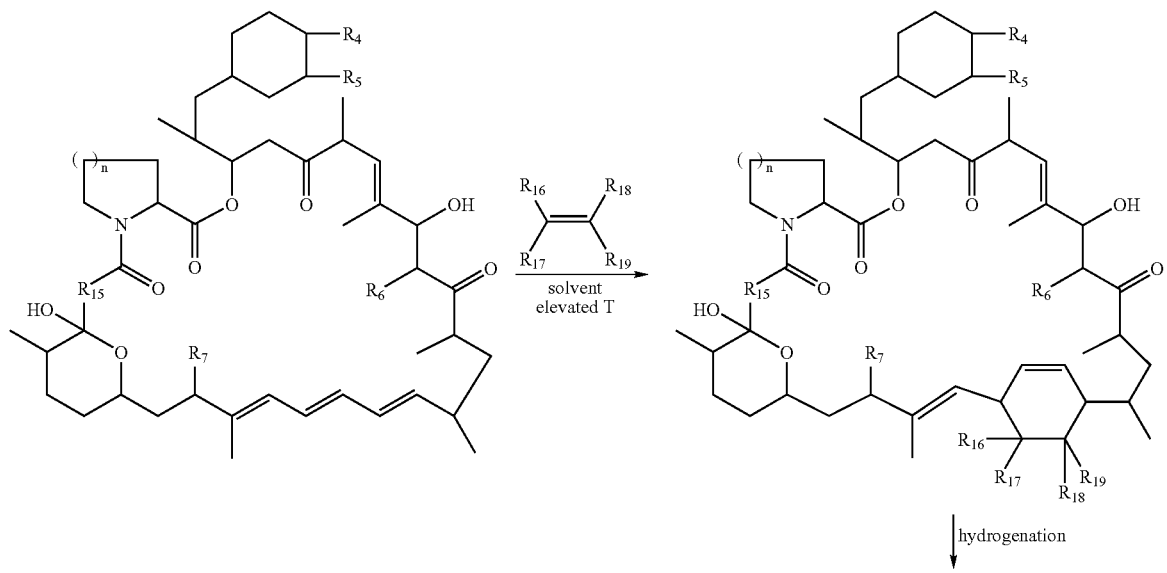

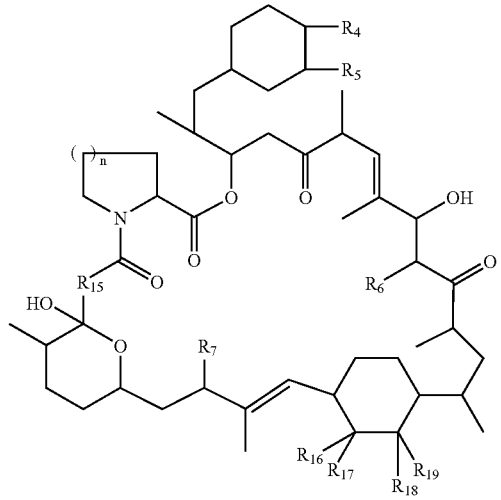

where $R_4$-$R_7$, $R_{15}$-$R_{19}$, and n are defined above.

The rapamycin derivatives of the present invention can be utilized in the form of pharmaceutically acceptable salts, prodrugs, or metabolites thereof derived from pharmaceutically or physiologically acceptable acids or bases. These salts include, but are not limited to, the following salts with mineral or inorganic acids such as hydrochloric acid, sulfuric acid, nitric acid, phosphoric acid and organic acids such as acetic acid, oxalic acid, succinic acid, and maleic acid. Other salts include salts with alkali metals or alkaline earth metals, such as sodium, potassium, calcium or magnesium in the form of esters, carbamates and other conventional "pro-drug" forms, which, when administered in such form, convert to the active moiety in vivo.

III. Methods of Using the Compounds of the Present Invention

The rapamycin derivatives of formula I of the present invention, including the more and less saturated rapamycin derivatives, have use in a variety of applications and include those relating to neurological disorders. The compounds of the present invention are useful in treating neurological disorders including, but not limited to, Alzheimer's disease amyotrophic lateral sclerosis, epilepsy, Huntington's Disease. Parkinson's Disease, stroke, spinal cord injury, traumatic brain injury, Lewy body dementia, multiple sclerosis, Pick's disease, Niewmann-Pick disease, amyloid angiopathy, cerebral amyloid angiopathy, systemic amyloidosis, hereditary cerebral hemorrhage with amyloidosis of the Dutch type, inclusion body myositis, mild cognitive impairment and Down's syndrome, and in the preparation of medicaments therefor. The rapamycin derivatives are also useful in treating complications due to stroke, head trauma, or spinal injury, or other injuries to the brain, peripheral nervous, central nervous, or neuromuscular system, and in the preparation of medicaments therefor.

The novel rapamycin derivatives are useful as neuroprotective agents. The rapamycin derivatives of the present invention may also be useful as neuroregenerative agents, i.e. restoring some neurological and/or neuromuscular or other function following onset of one of the above conditions and/or injury, stroke, or other trauma, and in the preparation of medicaments therefore.

The dosage requirements of the rapamycin derivatives of the present invention can vary depending on the condition, severity of the symptoms presented and the particular subject being treated. One of skill in the art would readily be able to determine the amount of the rapamycin derivative required. In one embodiment, about 0.5 to 200 mg is administered. In a further embodiment, about 0.5 to 100 mg is administered. In another embodiment, about 0.5 to about 75 mg is administered. In yet a further embodiment, about 1 to about 25 mg is administered. In another embodiment, about 0.5 to about 10 mg is administered, particularly when used in combination with another agent. In yet a further embodiment, about 2 to about 5 mg is administered. In yet another embodiment, about 5 to about 15 mg is administered.

Treatment can be initiated with dosages of the rapamycin derivative smaller than those required to produce a desired effect and generally less than the optimum dose of the rapamycin derivative. Thereafter, the dosage can be increased until the optimum effect under the circumstances is reached. Precise dosages will be determined by the administering physician based on experience with the individual subject being treated. In general, the compositions of this invention are most desirably administered at a concentration that will generally afford effective results without causing any harmful or deleterious side effects.

IV. Methods of Preparing Administrable Compositions Containing the Rapamycin Derivatives In one aspect, the present invention includes methods of preparing a pharmaceutical composition containing one or more rapamycin derivatives of the present invention. The composition can be administered to a mammalian subject by several different routes and is desirably administered orally in solid or liquid form.

Solid forms, including tablets, capsules, and caplets, containing the rapamycin derivative can be formed by blending the rapamycin derivative with one or more of the components described above. In one embodiment, the components of the composition are dry or vet blended. In another embodiment, the components are dry granulated. In a further embodiment, the components are suspended or dissolved in a liquid and added to a form suitable for administration to a mammalian subject.

Liquid forms containing the rapamycin derivative can be formed by dissolving or suspending the rapamycin derivative in a liquid suitable for administration to a mammalian subject.

Compositions containing the rapamycin derivative of the present invention can be prepared according to the present invention by combining the rapamycin derivative and a pharmaceutically acceptable carrier.

The compositions described herein containing the rapamycin derivative can be formulated in any form suitable for the desired route of delivery using a pharmaceutically effective amount of the rapamycin derivative. For example, the compositions of the invention can be delivered by a route such as oral, dermal, transdermal, intrabronchial, intranasal, intravenous, intramuscular, subcutaneous, parenteral, intraperitoneal, intranasal, vaginal, rectal, sublingual, intracranial, epidural, intratracheal, or by sustained release. In one embodiment, delivery is oral.

The oral dosage tablet composition of this invention can also be used to make oral dosage tablets containing analogs of the rapamycin derivative, including, but not limited to, esters, carbamates, sulfates, ethers, oximes, carbonates, and the like which are known to those of skill in the art.

A pharmaceutically effective amount of the rapamycin derivative can vary depending on the specific compound(s), mode of delivery, severity of the condition being treated, and any other active ingredients used in the composition. The dosing regimen can also be adjusted to provide the optimal therapeutic response. Several divided doses can be delivered daily, e.g., in divided doses 2 to 4 times a day, or a single dose can be delivered. The dose can however be proportionally reduced or increased as indicated by the exigencies of the therapeutic situation. In one embodiment, the delivery is on a daily, weekly, or monthly basis. In another embodiment, the delivery is on a daily delivery. However, daily dosages can be lowered or raised based on the periodic delivery.

The rapamycin derivatives of the present invention can be combined with one or more pharmaceutically acceptable carriers or excipients including, without limitation, solid and liquid carriers which are compatible with the compositions of the present invention. Such carriers include adjuvants, syrups, elixirs, diluents, binders, lubricants, surfactants, granulating agents, disintegrating agents, emollients, metal chelators, pH adjustors, surfactants, fillers, disintegrants, and combinations thereof, among others. In one embodiment, the rapamycin derivative is combined with metal chelators, pH adjustors, surfactants, fillers, disintegrants, lubricants, and binders.

Adjuvants can include, without limitation, flavoring agents, coloring agents, preservatives, and supplemental antioxidants, which can include vitamin E, ascorbic acid, butylated hydroxytoluene (BHT) and butylated hydroxyanisole (BHA).

Binders can include, without limitation, cellulose, methylcellulose, hydroxymethylcellulose, carboxymethylcellulose calcium, carboxymethylcellulose sodium, hydroxypropylcellulose, hydroxypropylmethylcellulose phthalate, microcrystalline cellulose, noncrystalline cellulose, polypropylpyrrolidone, polyvinylpyrrolidone (povidone, PVP), gelatin, gum arabic and acacia, polyethylene glycols, starch, sugars such as sucrose, kaolin, dextrose, and lactose, cholesterol, tragacanth, stearic acid, gelatin, casein, lecithin (phosphatides), cetostearyl alcohol, cetyl alcohol, cetyl esters wax, dextrates, dextrin, glyceryl monooleate, glyceryl monostearate, glyceryl palmitostearate, polyoxyethylene alkyl ethers, polyoxyethylene castor oil derivatives, polyoxyethylene stearates, polyvinyl alcohol, and gelatin, among others. In one embodiment, the binder is povidone, hydroxypropylmethylcellulose, carboxymethylcellulose, or gelatin. In another embodiment, the binder is povidone.

Lubricants can include magnesium stearate, light anhydrous silicic acid, talc, stearic acid, sodium lauryl sulfate, and sodium stearyl furamate, among others. In one embodiment, the lubricant is magnesium stearate, stearic acid, or sodium stearyl furamate. In another embodiment, the lubricant is magnesium stearate.

Granulating agents can include, without limitation, silicon dioxide, microcrystalline cellulose, starch, calcium carbonate, pectin, crospovidone, and polyplasdone, among others.

Disintegrating agents or disintegrants can include croscarmellose sodium, starch, carboxymethylcellulose, substituted hydroxypropylcellulose, sodium bicarbonate, calcium phosphate, calcium citrate, sodium starch glycolate, pregelatinized starch or crospovidone, among others. In one embodiment, the disintegrant is croscarmellose sodium.

Emollients can include, without limitation, stearyl alcohol, mink oil, cetyl alcohol, oleyl alcohol, isopropyl laurate, polyethylene glycol, olive oil, petroleum jelly, palmitic acid, oleic acid, and myristyl myristate.

Surfactants can include polysorbates, sorbitan esters, poloxamer, or sodium lauryl sulfate. In one embodiment, the surfactant is sodium lauryl sulfate.

Metal chelators can include physiologically acceptable chelating agents including edetic acid, malic acid, or fumaric acid. In one embodiment, the metal chelator is edetic acid.

pH adjusters can also be utilized to adjust the pH of a solution containing the rapamycin derivative to about 4 to about 6. In one embodiment, the pH of a solution containing the rapamycin derivative is adjusted to a pH of about 4.6. pH adjustors can include physiologically acceptable agents including citric acid, ascorbic acid, fumaric acid, or malic acid, and salts thereof. In one embodiment, the pH adjuster is citric acid.

Fillers that can be used according to the present invention include anhydrous lactose, microcrystalline cellulose, mannitol, calcium phosphate, pregelatinized starch, or sucrose. In one embodiment, the filler is anhydrous lactose. In another embodiment, the filler is microcrystalline cellulose.

In one embodiment, compositions containing the rapamycin derivative of the invention are delivered orally by tablet, caplet or capsule, microcapsules, dispersible powder, granule, suspension, syrup, elixir, and aerosol. In a further embodiment, when compositions containing the rapamycin derivative are delivered orally, delivery is by tablets and hard- or liquid-filled capsules.

In another embodiment, the compositions containing the rapamycin derivative can be delivered intravenously, intramuscularly, subcutaneously, parenterally and intraperitoneally in the form of sterile injectable solutions, suspensions, dispersions, and powders which are fluid to the extent that easy syringe ability exits. Such injectable compositions are sterile and stable under conditions of manufacture and storage, and free of the contaminating action of microorganisms such as bacteria and fungi.

In a further embodiment, compositions containing the rapamycin derivative can be delivered rectally in the form of a conventional suppository.

In another embodiment, compositions containing the rapamycin derivative can be delivered vaginally in the form of a conventional suppository, cream, gel, ring, or coated intrauterine device (IUD).

In yet another embodiment, compositions containing the rapamycin derivative can be delivered intranasally or intrabronchially in the form of an aerosol.

The rapamycin derivatives are administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, nonionic surfactants and edible oils such as corn, peanut and sesame oils, as are appropriate to the nature of the active ingredient and the particular form of administration desired. Adjuvants customarily employed in the preparation of pharmaceutical compositions are advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Similarly, oral administration of the compounds is preferred.

The rapamycin derivatives are also administered parenterally or intraperitoneally. Solutions or suspensions of these active compounds as a free base or pharmacologically acceptable salt are prepared in water suitably mixed with a surfactant such as hydroxypropylcellulose. Dispersions are also prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form is sterile and fluid to the extent that easy syringe ability exits. It is stable under conditions of manufacture and storage and is preserved against the contaminating action of microorganisms such as bacterial and fungi. The carrier is a solvent or dispersion medium containing, for example, water, ethanol (e.g., glycerol, propylene glycol and liquid polyethylene glycol), suitable mixtures thereof, and vegetable oil.

V. Kits of the Invention

The present invention also provides kits or packages containing the rapamycin derivatives. Kits of the present invention can include the rapamycin derivative of the present invention and a carrier suitable for administration to a mammalian subject as discussed above. The kits can also contain the reagents required to prepare the rapamycin derivatives of the present invention and include a rapamycin, an optionally substituted olefin, and a solvent.

The kits can optionally include other reagents to form other rapamycin derivatives and include hydrogenation agents.

The kit can further contain instructions for performing the reactions of the present invention. Also provided in a kit can be other suitable chemicals, disposable gloves, decontamination instructions, applicator sticks or containers, and sample preparator cups.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLES

Example 1

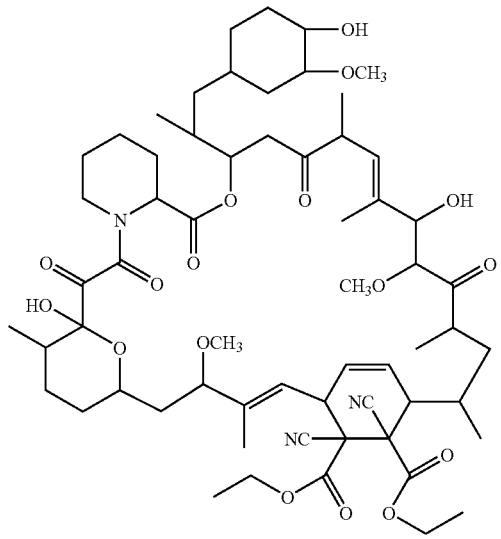

Rapamycin (0.25 g, 0.274 mmol) is dissolved in 5 ml solvent with gentle heating. To this solution is added, dropwise, a solution of diethyl dicyanofumarate (0.183 g, 3 eq) in 7 mL solvent. The reaction mixture is stirred at 50 to 80° C. for 12 to 36 hours, and then the reaction mixture is via reversed-phase HPLC to yield the product.

Example 2

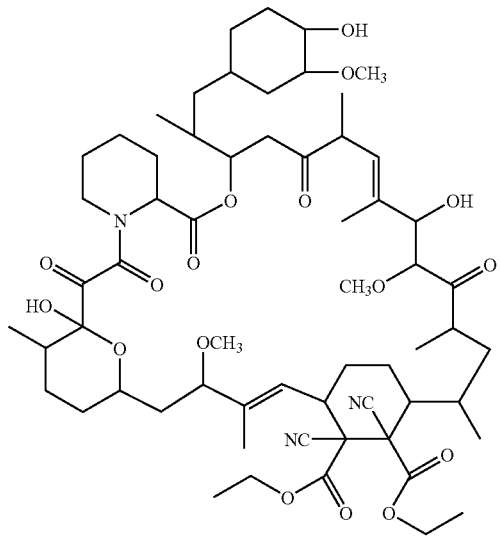

The compound prepared according to Example 1 is dissolved in methanol in a 18 mm test-tube, and a spatula tip of Pd/C catalyst (Aldrich) is added. The mixture is hydrogenated on a Parr apparatus for 15 minutes at 2.0 atmosphere $H_2$. The products are chromatographed via reversed-phase HPLC to yield give the product.

Example 3

Mescencephalic dopaminergic neuron cultures are prepared as described in Pong et al., J. Neurochem. 69: 986-994, 1997, which is incorporated herein by reference in its entirety. Embryonic day 15 (E15) rat fetuses are collected and dissected in ice-cold phosphate-buffered saline (PBS). The ventral piece of tissue compromising the mesencephalic dopaminergic region is dissected out. Dissected pieces of tissue are pooled together and transferred to an enzymatic dissociation medium containing 20 IU/mL papain in Earle's balanced salt solution (Worthington Biochemical, Freehold, N.J., USA) and incubated for 60 minutes at 37° C. After enzymatic dissociation, the papain solution is aspirated and the tissue mechanically triturated with a fire-polished glass Pasteur pipette in complete medium (equal volumes of minimum essential medium (MEM) and F-12 nutrient mixture (GibcoBRL) supplemented with 0.1 mg/ml apotransferrin and 2.5 µg/mL insulin) containing 2,000 IU/mL DNase and 10 mg/mL ovomucoid protease inhibitor.

For dopamine uptake experiments, single-cell suspensions complete media are seeded on poly-L-ornithine and laminin coated 24-well plates. The cultures are maintained for seven days prior to experimentation. Cultures are pretreated with various concentrations of the compound for 24 hours, then exposed to 10 mM MPP+ for 1 hour. Following the 1 hour incubation, media is exchanged three times and fresh compound is added for an additional 48 hours.

After 48 hours growth of mesencephalic dopaminergic neuron cultures following MPP+ exposure, high-affinity 3H-dopamine uptake is performed using a modified method described by Prochiantz et al., Nature 293: 570-572, 1981, which is incorporated herein by reference. Cultures are washed with pre-warmed PBS containing 5.6 mM glucose and 1 mM ascorbic acid. Cultures are then incubated for 15 minutes at 37° C. with 50 nM 3H-dopamine (31 Ci/mmol, DuPont-NEN, Wilmington, Del., USA). The cultures are washed twice with buffer and lysed with 0.5 N NaOH. The lysate is transferred to a scintillation vial containing Ultima Gold™ scintillation cocktail and radioactivity is determined with a liquid scintillation counter. Alternatively, culture lysates are washed twice with buffer, incubated for 2 hours at room temperature with Optiphase Supermix™ scintillation cocktail (Wallac Scintillation Products, Gaithersburg, Md., USA), and radioactivity measured with a liquid scintillation counter.

Dissociated cortical neuron cultures are prepared as previously described (Pong et al., 2001). Briefly, embryonic day 15 rat fetuses are collected and dissected in ice-cold PBS. Dissected cortices are pooled together and transferred to an enzymatic dissociation medium containing papain. After 30 minutes, the tissue is mechanically triturated with a fire-polished glass Pasteur pipette. Single-cell suspensions in complete media are seeded on poly-L-ornithine and laminin coated 96-well plates. After 24 hours, cultures are treated with various concentrations of compound for 72 hours. The cultures are then fixed and stained with an anti-tubulin primary antibody (TUJ-1) and a fluorescent-tagged secondary antibody. Neurite outgrowth is determined by using the Enhanced Neurite Outgrowth (ENO) algorithm with the Cellomics ArrayScan and expressed as average neurite length or total neurite length per cell.

The compounds of Example 1 and 2 are anticipated to be active in cortical neuron assays with an $EC_{50}$ less than 1 µM an active in dopaminergic uptake assays with an $EC_{50}$ less than 1 µM.

All patent, patent publications, and other publications listed in this specification are incorporated herein by reference. While the invention has been described with reference to a particularly preferred embodiment, it will be appreciated that modifications can be made without departing from the spirit of the invention. Such modifications are intended to fall within the scope of the appended claims.

What is claimed is:

1. A compound of the formula I:

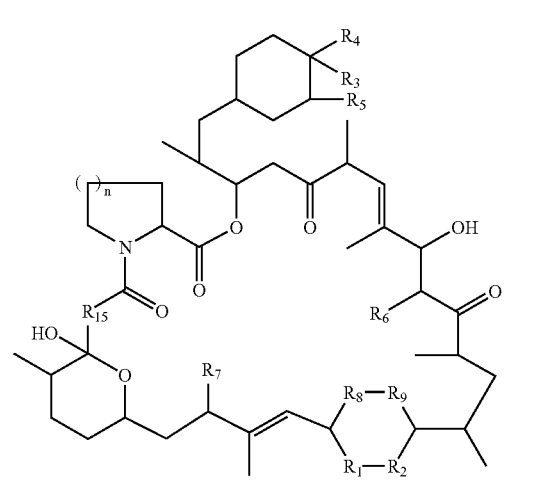

wherein:
$R_1$ and $R_2$ are the same or different and are selected from the group consisting of $CR_{16}R_{17}$ and $CR_{18}R_{19}$;
$R_3$ and $R_4$ are:
(a) independently selected from the group consisting of H, OH, O($C_1$ to $C_6$ alkyl), O(substituted $C_1$ to $C_6$ alkyl), O(acyl), O(aryl), O(substituted aryl), and halogen; or
(b) taken together to form a double bond to O;
$R_5$, $R_6$, and $R_7$ are independently selected from the group consisting of H, OH, and $OCH_3$;
$R_8$ and $R_9$ are connected though a (i) single bond and are $CH_2$ or (ii) double bond and are CH;
$R_{15}$ is selected from the group consisting of C=O, CHOH, and $CH_2$;
$R_{16}$ and $R_{17}$ are independently selected from the group consisting of H, $C_1$ to $C_6$ alkyl, $C_1$ to $C_6$ substituted alkyl, aryl, substituted aryl, acyl, $CF_3$, CN, and $NO_2$;
$R_{18}$ and $R_{19}$ are independently selected from the group consisting of H, $C_1$ to $C_6$ alkyl, $C_1$ to $C_6$ substituted alkyl, aryl, substituted aryl, acyl, $CF_3$, CN, and $NO_2$; or
$R_{17}$ and $R_{18}$ are taken together to form a monocyclic, saturated, partially unsaturated, or wholly unsaturated 5- to 7-membered ring optionally containing one to 4 heteroatoms independently selected from N, S and O;
n is 1 or 2;
wherein the acyl group is HC(O)— or a —C(O)R'''— group, wherein R''' is selected from the group consisting of alkyl, substituted alkyl, and alkoxy;
wherein the substituents for the substituted alkyl, aryl, or acyl consist of one or more substituents independently selected from the group consisting of halogen, CN, OH, $NO_2$, amino, aryl, a heterocyclic ring consisting of a monocyclic, saturated, partially unsaturated, or wholly unsaturated 4- to 7-membered ring having 1 to 4 heteroatoms independently selected from N, S and O, alkoxy, aryloxy, alkylcarbonyl, alkylcarboxy, and arylthio;

or a pharmaceutically acceptable salt thereof.

2. The compound according to claim 1, wherein $R_{17}$ and are taken together to form the 5- to 7-membered ring.

3. The compound according to claim 1, wherein $R_8$ and $R_9$ are bound through a single bond.

4. The compound according to claim 1, wherein $R_3$ or $R_4$ is OH.

5. The compound according to claim 1, wherein $R_3$ or $R_4$ is O(acyl).

6. The compound according to claim 5, wherein said acyl is:

[Structure of acyl group with pyridine]

7. The compound according to claim 1, wherein $R_5$, $R_6$, and $R_7$ are $OCH_3$.

8. The compound according to claim 1, wherein n is 2.

9. The compound according to claim 1, wherein $R_{15}$ is C=O.

10. A compound of the formula Ia:

[Structure Ia]

wherein:
$R_1$ and $R_2$ are the same or different and are selected from the group consisting of $CR_{16}R_{17}$ and $CR_{18}R_{19}$;

$R_6$ is selected from the group consisting of H, OH, and $OCH_3$;

$R_8$ and $R_9$ are connected through a (i) single bond and are $CH_2$ or (ii) double bond and are CH;

$R_{16}$ and $R_{17}$ are independently selected from the group consisting of H, $C_1$ to $C_6$ alkyl, $C_1$ to $C_6$ substituted alkyl, aryl, substituted aryl, acyl, $CF_3$, CN, and $NO_2$;

$R_{18}$ and $R_{19}$ are independently selected from the group consisting of H, $C_1$ to $C_6$ alkyl, $C_1$ to $C_6$ substituted alkyl, aryl, substituted aryl, acyl, $CF_3$, CN, and $NO_2$; or $R_{17}$ and $R_{18}$ are taken together to form a monocyclic, saturated, partially unsaturated, or wholly unsaturated 5- to 7-membered ring optionally containing one to 4 heteroatoms selected from N, S and O;

wherein the acyl group is HC(O)— or —C(O)R'''—, wherein R''' is selected from the group consisting of alkyl, substituted alkyl, and alkoxy;

or a pharmaceutically acceptable salt thereof.

11. A compound having the structure

[Structure]

or a pharmaceutically acceptable salt thereof.

12. A compound having the structure

[Structure]

or a pharmaceutically acceptable salt thereof.

13. A method of preparing a compound as defined in claim 1, or a pharmaceutically acceptable salt thereof, comprising reacting rapamycin or an analog thereof with an olefin of formula $R_{16}R_{17}C=CR_{18}R_{19}$ to give a compound as defined in claim 1 wherein $R_8$ and $R_9$ are connected through a double bond and are CH, and if desired, hydrogenating to give a compound as defined in claim 1 wherein $R_8$ and $R_9$ are connected through a single bond and are $CH_2$, and further if desired, isolating as a pharmaceutically acceptable salt thereof.

14. The method according to claim 13, wherein said rapamycin analog is norrapamycin, deoxorapamycin, or desmethylrapamycin.

15. The method according to claim 13, wherein the reaction is performed at elevated temperatures.

16. The method according to claim 13, wherein the product is isolated using chromatography.

17. The method according to claim 13, wherein the hydrogenation is carried out using a Pd/C catalyst and hydrogen gas.

18. The method according to claim 13, wherein the product has formula I wherein $R_8$ and $R_9$ are connected through a single bond and are $CH_2$, or a pharmaceutically acceptable salt thereof.

* * * * *